United States Patent [19]

Qian et al.

[11] Patent Number: 6,077,846
[45] Date of Patent: *Jun. 20, 2000

[54] EPIBATIDINE AND DERIVATIVES THEREOF AS CHOLINERGIC RECEPTOR AGONISTS AND ANTAGONISTS

[75] Inventors: Changgeng Qian, Wayland; Tongchuan Li, Framingham, both of Mass.; Tesfaye Biftu, Westfield, N.J.; Tsung-Ying Shen, Great Falls, Va.

[73] Assignee: UCB, S.A., Brussels, Belgium

[*] Notice: This patent is subject to a terminal disclaimer.

[21] Appl. No.: 08/612,964

[22] PCT Filed: Sep. 9, 1994

[86] PCT No.: PCT/US94/10121

§ 371 Date: Dec. 17, 1996

§ 102(e) Date: Dec. 17, 1996

[87] PCT Pub. No.: WO95/07078

PCT Pub. Date: Mar. 16, 1995

Related U.S. Application Data

[63] Continuation of application No. 08/119,697, Sep. 10, 1993, abandoned.

[51] Int. Cl.$^7$ ............................................. A61K 31/44
[52] U.S. Cl. ............................................. 514/299
[58] Field of Search ............................................. 514/299

[56] References Cited

U.S. PATENT DOCUMENTS

| | | | |
|---|---|---|---|
| 4,835,162 | 5/1989 | Abood | 514/305 |
| 4,910,193 | 3/1990 | Buchheit . | |
| 4,940,703 | 7/1990 | Baker et al. | 514/210 |
| 4,966,916 | 10/1990 | Abood | 514/534 |
| 4,992,436 | 2/1991 | Baker et al. | 514/215 |
| 5,104,989 | 4/1992 | Cottrell et al. | 546/112 |
| 5,106,853 | 4/1992 | Showell et al. | 514/299 |
| 5,124,460 | 6/1992 | Humphrey | 548/131 |
| 5,128,118 | 7/1992 | Carroll et al. . | |
| 5,219,860 | 6/1993 | Chambers et al. | 514/278 |
| 5,227,385 | 7/1993 | Caldwell et al. . | |
| 5,242,927 | 9/1993 | Baker et al. | 514/299 |
| 5,242,930 | 9/1993 | Baker et al. | 514/305 |
| 5,256,671 | 10/1993 | Ladduwahetty et al. | 514/305 |
| 5,260,293 | 11/1993 | Baker et al. | 514/214 |
| 5,288,730 | 2/1994 | Baker et al. | 514/305 |
| 5,314,899 | 5/1994 | Daly et al. | 514/339 |
| 5,324,723 | 6/1994 | Baker et al. | 514/212 |
| 5,405,853 | 4/1995 | Baker et al. | 514/299 |
| 5,426,106 | 6/1995 | Kulagowski et al. | 514/233 |
| 5,432,177 | 7/1995 | Baker et al. | 514/253 |
| 5,444,074 | 8/1995 | Baker et al. | 514/326 |
| 5,451,588 | 9/1995 | Baker et al. | 514/323 |
| 5,459,270 | 10/1995 | Williams et al. | 546/152 |
| 5,461,063 | 10/1995 | Kelleher et al. | 514/312 |

FOREIGN PATENT DOCUMENTS

| | | |
|---|---|---|
| 6-312989 | 11/1994 | Japan . |
| 7010878 | 1/1995 | Japan . |
| WO 93/18037 | 9/1993 | WIPO . |
| WO 94/04152 | 3/1994 | WIPO . |
| WO 94/07489 | 4/1994 | WIPO . |
| WO 94/22868 | 10/1994 | WIPO . |
| WO 95/07078 | 3/1995 | WIPO . |
| WO 96/06093 | 2/1996 | WIPO . |

OTHER PUBLICATIONS

Abstracts of Poster Presentations Nos. 1–97, "The Otto Loewi New Investigator Awards for 1995," *Life Sciences*, 56(11/12):1001–1050 (1995).

Adamus, et al., "Phase I Clinical Trials with WAL2014, A New Muscarinic Agonist for the Treatment of Alzheimer's Disease," *Life Sciences*, 56:(11/12):883–890 (1995) (Elsevier Sciences, Ltd., Editors).

Ainsworth, et al., "Alkyl–1,3,4–oxadiazoles," *J. Org. Chem.*, 31:3442–3444 (1966).

Altenbach, H.J., et al., "7–Azanorbornadiene," *Angew Chem. Int. Ed. Engl.*, 21(10):778 (1992).

Altenbach, H.J., et al., "Synthesis and Photoelectron Spectra of 7–Azanorbornadiene and Related Compounds. An Analysis with Fragment Orbitals," *Chem. Ber.* 124:791–801 (1991).

Badio and Daly, "Epibatidine, a Potent Analgetic and Nicotinic Agonist," *Mol. Pharmacol.*, 45:563–569 (1994).

Badio and Daly, "Epibatidine. A potent analgetic and nicotinic agonist," *FASEB Journal*, 8(4–5):A875 (1994).

Baker and Saunders, "Central Muscarinic Ligands and Receptors," *Ann. Rep. in Med. Chem.* Chapter 4, 24:31–39 (1989).

Bansal, et al., "Influence of Lewis acids on the Diels–Alder reaction. Part I. An improved synthesis of 7–azanorbornadiene, 3–azaquadricyclaine, and azepine derivatives," *Can. J. Chem.*, 47:2391–2394 (1969).

Barber, and Gottschlich, "Opioid Agonists and Antagonists: An Evaluation of Their Peripheral Actions in Inflammation," *Medicinal Research Review*, 12(5):525–562 (1992).

Barnes, et al., "Tiotropium Bromide (Ba 679 BR), a Novel, Long–Acting Muscarinic Antagonists for the Treatment of Obstructive Airways Disease," *Life Sciences*, 56:(11/12):853–859 (1995) (Elsevier Science, Ltd., Editors).

Bhattacharya, S.N., et al., "Friedel–Crafts Sulphonylation of Bis(trimethylsilyl)acetylene: a Useful Route to Aryl Ethynyl Sulphones," *Organomet. Chem. Synth.*, 1:145–149 (1970).

Bittoun, "Recurrent aphthous ulcers and nicotine," *Med. J. Australia*, 154:471–472 (1991).

Bradley, "Frog Venom Cocktail Yields A One–Handed Painkiller," *Science* 261:1117 (1993).

Broka, C.A., "Total Synthesis of Epibatidine," *Tet. Lett.*, 34(20):3251–3254 (1993).

(List continued on next page.)

*Primary Examiner*—William R. A. Jarvis
*Attorney, Agent, or Firm*—McDonnell Boehnen Hulbert & Berghoff

[57] ABSTRACT

This invention relates to the treatment of conditions that can be treated with a nicotinic agonist by administering to a patient an effective amount of a 7-azabicyclo[2.2.1]-heptane or heptene. Specific conditions that may be treated include excess body weight, ulcerative colitis, aplthous ulcer, smoking, Parkinson's Disease, Alzeimer's Disease, and Tourette's Syndrome

10 Claims, 5 Drawing Sheets

OTHER PUBLICATIONS

Burgen, "The Background of the Muscarinic System," *Life Sciences*, 56(11/12):801–806 (1995) (Elsevier Science, Ltd., Editors).

Burke, et al., "Construction of a Molecular Shape Analysis–Three–Dimensional Quantitative Structure–Analysis Relationship for an Analog Series of Pyridobenzodiazepinone Inhibitors of Muscarinic 2 and 3 Receptors," *J. Med. Chem.*, 37:3775–3788 (1994).

Carroll, et al., "3–Aryl–2–(3'–substituted–1',2',4'–oxidiazol–5'–yl)tropane Analogues of Cocaine: Affinities at the Cocaine Binding Site at the Dopamine, Serotonin, and Norepinephrine Transporters," *J. Med. Chem.*, 36: 2886–2890 (1993).

Chen, et al., "Synthesis of the Epibatidine Ring System from Pyrroles via Their Pentaammineosmium(II) Complexes," *Am. Chem. Soc. Meeting*, Denver, Colorado (Mar. 28–Apr. 2), 1993.

Christensen, et al., "Antinociceptive effects of the stereoisomers of nicotine given intrathecally in spinal rats," *J. Neural Transm. GenSec.*, 80:189–194 (1990).

Clayton and Regan, "A Total Synthesis of (+/–) Epibatidine," *Tetrahedron Letters*, 34(46):7493–7496 (1993).

Cooley, et al., "Effect of pCPA on Nicotine–Induced Analgesia," *Pharmacol. Biochem. Behav.*, 36:413–415 (1990).

Cordone, R., et al., "$\pi$–Heterocyclic Complexes of Pentaammineosmium(II) and the Metal–Induced Cycloaddition of Pyrrole and Maleic Anhydride," *J. Am. Chem. Soc.*, 111:5969–5970 (1989).

Corey, E.J., et al., "Stereocontrolled Total Synthesis of (+)– and (–)– epibatidine," *J. Org. Chem.*, 58:(21):5600–5602 (1983).

Corey, et al., "A Synthetic Method for Formyl–Ethynyl Conversion (RCHO–>RC=CH or RC =CR)," *Tetrahedron Letters*, 36:3769–3772 (1972).

Daly, et al., "A New Class of Indolizidine Alkaloids from the Poison Frog, *Dendrobates tricolor*. X–ray Analysis of 8–Hydroxy–8–methyl–6–(2'–methylhexylidine)–1–azabicyclo[4.3.0]nonane," *J. Am. Chem. Soc.*, 102:830–836 (1980).

Davis and Whitham, "Ethynyl p–Tolyl Sulphone as an Acetylene Equivalent in Diels–Alder Reactions," *J.C.S. Chem. Comm.*, pp. 639 (1980).

Devor and Isenberg, "Nicotine and Tourette's Syndrome," *Lancet*, 2:1046 (1989).

Donnini and Just, "Diels–Alder Reactions of Pyrroles as an Entry to Substituted 3–Oxatropanes and Tetrasubstituted Pyrrolidines," *Heterocycl. Chem.*, 14:1423–1425 (1977).

Drew, et al., "High–pressure Synthesis, Structures, and Conformational Properties of Some Derivatives of 7–Azabicyclo[2.2.1]heptane. X–Ray Determination of endo–10–Benzoyl–4–phenyl–4,10–diazatricyclo[5.2.1.0$^{2,6}$] dec–8–ene–3,5–dione and exo–10–Acetyl–4–phenyl–4, 10–diazatricyclo[5.2.1.0$^{2,6}$]decane–3,5–dione," *J.C.S. Perkins Trans.* I:1277–1284 (1985).

Dukat, M.; et al., "Epibatidine: A very high affinity nicotine–receptor ligand," *Medicinal Chem. Res.*, 4:131–139 (1994).

Duvoisin, "Cholinergic–Anticholinergic Antagonism in Parkinsonism," *Arch. Neurol.* 17:124–136 (1967).

Ehlert and Thomas, "Functional Role of $M_2$ Muscarinic Receptors in the Guinea Pig Ileum," *Life Sciences*, 56(11/12):965–971 (1995) (Elsevier Science, Ltd., Editors).

Ehringer and Hornykiewicz, "Verteilung Von Noradrenalin Und Dopamin (3–Hydroxytyramin) Im Gehirn Des Menschen Und Ihr Verhalten Bei Erkrankungen Des Extrapyramidalen Systems," *Klin. Wochenschr.*, 38:1236–1239 (1960).

Feriani, et al., "Cholinergic Agents Structurally Related to Furtrethonium. 2. Synthesis and Antimuscarinic Activity of a Series of N–[5–[(1'–Substituted–acetoxy)methyl]–2–furfuryl]dialkylamines," *J. Med. Chem.*, 37:4278–4287 (1994).

Fisher, et al., "Epibatidine, An Alkaloid From the Poison Frog *Epipedobates tricolor*, Is a Powerful Ganglionic Depolarizing Agent," *J. of Pharm. and Exp. Therap.* 270:702–707 (1994).

Fitjer, et al., "The Wittig Reaction using Potassium–Tert–Butoxide High Yield Methylenations of Sterically Hindered Ketones," *Synthetic Communications*, 15(10):855–864 (1985).

Fletcher, et al., "The Synthesis of (+) and (–) Epibatidine," *J. Chem. Soc. Chem. Comm.*, 1216–1218 (1993).

Fletcher, S., et al., "Total synthesis and determination of the absolute configuration of epibatidine," *J. Org. Chem.*, 59(7):1771–1778 (1994).

Flynn, et al., "Differential Alterations in Mscarinic Receptor Subtypes in Alzheimer's Disease: Implications for Cholinergic–Based Therapies," *Life Sciences*, 56(11/12):868–876 (1995) (Elsivier Science, Ltd., Editors).

Fraser and Lee, "Regulation of Muscarinic Receptor Expression by Changes in mRNA Stability," *Life Science*, 56(11/12):899–906 (1995) (Elsevier Sciences, Ltd., Editors).

Fraser, et al., "Synthesis of 7–azabicyclo[2.2.1]heptane, exo–2–chloro–7–azabicyclo[2.2.1]heptane, and derivatives," *Can. J. Chem.*, 48:2065–2074 (1970).

Gabel, N.W., "Diels–Alder Reactions of 1–Carbomethoxy––pyrroles and Dimethyl cetylenedicarboxylate," *J. Org. Chem.*, 27:301–303 (1962).

Garvey, et al., "Novel Isoxazoles which Interact with Brain Cholinergic Channel Receptors Have Intrinsic Cognitive Enhancing and Anxiolytic Activities," *J. Med.Chem.*, 37:1055–1059 (1994).

Garvey, et al., "Synthesis and in Vitro Characterization of Novel Amino Terminally Modified Oxotremorine Derivatives for Brain Muscarinic Receptors," *J. Med. Chem.*, 35:1550–1557 (1992).

Glassman and Covey, "Future Trends in the Pharmacological Treatment of Smoking Cessation" *Drugs*, 40(1): 1–5 (1990).

Goldstein and Shen, "Dual Inhibitors of Platelet Activating Factor and 5–Lipoxygenase II. Novel 2,4–Diaryl–1,3–dithiolanes with Iron–Chelating Functionalities," *Med. Chem. Res.*, 2:451–456 (1992).

Goldstein and Shen, "Dual Inhibitors of Platelet Activating Factor and 5–Lipoxygenases I. 2,4–Diaryl–1,3–dithiolanes," *Med. Chem. Res.*, 2:443–450 (1992).

Gonzalez, J., et al., "Dearomatization of Analines via Complexation to Pentaammineosmium(II): A Novel [2+2+2] Michael–Ring–Closure Reaction of an $n^2$–Coordinated Analine," *Am. Chem. Soc. Mtg.*, 205th ACS National Meeting, Denver CO, Mar. 1993.

Gopalakrishnan and Sullivan, "Targeting Nicotinic Cholinergic Receptors," *Drug News & Perspectives*, 7(7):444–448 (1994).

Gourlay and McNeil, "Antismoking products," *Med. J. Australia*, 153:699–707 (1990).

Grunberg, et al., "Effects of nicotine on body weight and food consumption in rats," *Psychopharmacology*, 83:93–98 (1984).

Hacksell, et al., "Quinuclidin–2–ENE–Based Muscarinic Antagonists," *Life Sciences*, 56(11/12):831–836 (1995) (Elsevier Science, Ltd., Editors).

Hamilton, et al., "Molecular Analysis of the Regulation of Muscarinic Receptor Expression and Function," *Life Sciences*, 56:11/12):939–943 (1995) (Elsevier Science, Ltd., Editors).

Hersch and Levey, "Diverse Pre– and Post–Synaptic Expression of m1–m4 Muscarinic Receptor Proteins in Neurons and Afferents in the Rat Neostriatum," *Life Sciences*, 56(11/12):931–938 (1995) (Elsevier Science, Ltd., Editors).

Hille, et al., "Multiple G–Protein–Coupled Pathways Inhibit N–Type Ca Channels of Neurons," *Life Sciences*, 56(11/12):989–992 (1995) (Elsevier Science, Ltd., Editors).

Hirschberg, et al., "Kinetic and Biophysical Analysis of the m2 Muscarinic Receptor," *Life Sciences*, 56(11/12):907–913 (1995) (Elsevier Science, Ltd., Editors).

Hodges, L.M., et al., "$\eta^2$–Pyrrole Complexes as Synthons to Alkaloid Derivatives," *J. Org. Chem.*, 58:4788–4790 (1993).

Hosey, et al., "Multiple Mechanisms Involving Protein Phosphorylation are Linked to Desensitization of Muscarinic Receptors," *Life Sciences*, 56(11/12):951–955 (1995) (Elsevier Science, Ltd., Editors).

Huang and Shen, "A Versatile Total Synthesis of Epibatidine and Analogs," *Tet. Let.*, 34:4477–4480 (1993).

Huang, D.F., et al., "A Versatile Total Synthesis of Epibatidine and Analogs," *Tetrahedron Letters*, 58:28 4477–4480 (1993).

Hulme, et al., "The Role of Charge Interactions in Muscarinic Agonist Binding, and Receptor–Response Coupling," *Life Sciences*, 56(11/12):891–898 (1995) (Elsevier Science, Ltd., Editors).

Jacobi, et al. "Bis Heteroannulation. 2. Oxazole Alcohols from the Interaction of Lithiomethyl Isocyanide with Lactones. A Novel Synthesis of Evodone,", *J.Org. Chem.*, 46:2065–2069 (1981).

Jacobson, et al., "Molecular Probes for Muscarinic Receptors: Functionalized Congeners of Selective Muscarinic Antagonists," *Life Sciences*, 56(11/12):823–830 (1995) (Elsevier Science, Ltd., Editors).

Jaen, et al., "In Vitro and In Vivo Evaluation of the Sub-type–Selective Muscarinic Agonist PD 151832," *Life Sciences*, 56(11/12):845–852 (1995) (Elsevier Science, Ltd., Editors).

Janson, et al., "Chronic nicotine treatment partly protects against the 1–methyl–4–phenyl–2,3,6–tetrahydropyridine–induced degeneration of nigrostriatal dopamine neurons in the black mouse," *Acta Physiol. Scand.*, 132:589–591 (1988).

Janson, et al., "GM1 ganglioside protects against the 1–methyl–4–phenyl–1,2,3,6–tetrahydropyridine–induced degeneration of nigrostriatal neurons in the black mouse," *Acta Physiol. Scand.*, 132:587–588 (1988).

Jarvik, "Beneficial effects of nicotine," *Br. J. of Addiction* 86:571–575 (1991).

Jenden, et al., "Summary and Closing Comments," *Life Sciences*, 56(11/12):993–1000 (1995) (Elsevier Science, Ltd., Editors).

Jick et al., "Cigarette Smoking and Ulcerative Colitis," *N. Eng. J. Med.*, 308(5):261–263 (1983).

Julia and Paris, "Syntheses A L'Aide De Sulfones $V^{(+)}$–Methode De Synthese Generale de Doubles Liaisons," *Tetrahedron Letters*, 49:4833–4836 (1973).

Jung and Rohloff, "Intramolecular Diels–Alder Chemistry of Pyrroles," *J. Chem. Soc., Chem. Comm.* pp. 630–632 (1984).

Kadaba, "Role of Protic and Dipolar Aprotic Solvents in Heterocyclic Synthesis via 1,3–Dipolar Cycloaddition Ractions," *Synthesis*, 71–84 (1973).

Kaye and Soreff, "The Psychiatrists's Role, Responses, and Responsibilities When a Patient Commits Suicide," *Am. J. Psychiatry*, 148(6):739–743 (1991).

Kellar, "Epibatidine: Its Pharmacological Actions and Utility for Studying Neuronal Nicotinic Receptors," *Neurotransmissions*, XI(4):1–5 (1995).

Kilbinger, et al., "Prejunctional Muscarinic Receptors Regulating Neurotransmitter Release in Airways," *Life Sciences*, 56(11/12):981–987 (1995).

Kozikowsky and Li, "A Nitrile Oxide Based Entry to 2,3–Dihydropyran–4–ones. Synthesis of a Protected Version of "compactin Lactone" in Racemic and Optically Active Forms," *J. Org. Chem.*, 50:778–785 (1985).

Kotsuki, H., et al., "High–Pressure Reactions of Pyrroles with Dimethyl cetylenedicarboxylate," *Heterocycles*, 19:1915–1920 (1982).

Kricka and Vernon, "Nitrogen–Bridged Six–Membered Ring Systmes: 7–Azabicyclo[2.2.1]hepta–2,5–dienes, Naphthalen–I,4–imines, and Anthracen–9,10–imines," *Adv. in Heterocycl. Chem.*, 16: 87–121 (1974).

Krow, et al., "Homoepibatidines. syn–6– and syn–5(6–Chloro–3–pyridyl)isoquinuclidines. Potent Nicotinic Receptor Ligands," *Tetrahedron Letters* (In Press 1996).

Kuhar, M.J., et al. "3–β–(4–idophenyl–tropan–2–β–carboxylic acid methyl ester tartrate and Related Compounds as Cocaine Receptor–Binding Ligands," *Chem. Abstr.*, 116(7):447 (1992) 55131n.

Lambrecht, et al., "The Design and Pharmacology of Novel Selective Muscarinic Agonists and Antagonists," *Life Sciences*, 56(11/12):815–822 (1995) (Elsevier Science, Ltd., Editors).

Larock and Johnson, "Palladium–catalysed Intermolecular Arylation and Alkenylation of Bicyclic Alkenes," *J. Chem. Soc. Chem. Comm.*, 1368–1370 (1989).

Lashner et al., "Testing Nicotine Gum for Ulcerative Colitis Patients," *Digest. Dis. Sci.*, 35(7):827–832 (1990).

Lee, J.W. and Oh, D.Y., "Conversion of B–Oxo Sulfones into Acetylenic Sulfones," *Synlett*, p. 290 (1990).

Leroy, et al., "Synthesis of 3,4–Bis[trifluoromethyl]–1H–pyrrole," *Synthesis*, 313–315 (1982).

Li, et al., "The Analgesic Effect of Epibatidine and Isomers," *Bioorg. and Med. Chem. Letters*, 3:2759–2764 (1993).

Lichtensteiger, et al., "A Quantitative Correlation Between Single Unit Activity and Fluorescence Intensity of Dopamine Neurones in Zona Compacta of Substantia Nigra, as Demonstrated Under the Influence of Nicotine and Physostigmine," *Brain Res.*, 117:85–103 (1976).

Linde, et al., "Straightford Synthesis of 1,2,3–Tricarbonyl Systems," *J. Org. Chem.*, 56:2534–2538 (1991).

McPherson, et al., "Resolution and in Vitro and Initial in Vivo Evaluation of Isomers of Iodine–125–Labeled 1–Azabicyclo[2.2.2]oct–3–yl a–Hydroxy–a–(1–iodo–1–propen–3–yl)–a–phenylacetate: A High–Affinity Ligand for the Muscarinic Receptor," *J. Med. Chem.*, 38:3908–3917 (1995).

Melchiorre, et al., "The Design of Novel Methoctramine–Related Tetraamines as Muscarinic Receptor Subtype Selective Antagonists," *Life Sciences*, 56(11/12):837–844 (1995) (Elsevier Science, Ltd., Editors).

Moll, *Brit Med. J.*, 1: 1079 (1926).

Moss et al., "Nicotine and Cannabinoids as Adjuncts to Neuroleptics in the Treatment of Tourette Syndrome and Other Motor Disorders," *Life Sciences*, 44:1521–1525 (1989).

Myers, W.H., et al., "Tautomerizations, Protonations, and Electrophilic Additions of $n^2$–Coordinated Pyrroles," *J. Am. Chem. Soc.*, 114(14):5684–5692 (1992).

Numa et al., "Molecular Structure of the Nicotinic Acetylcholine Receptor," Cold Spring Harbor Symp. Quant. Biol., 48:57–69 (1983).

Onali and Olianas, "Bimodal Regulation of cyclic Amp by Muscarinic Receptors Involvement of Multiple G Proteins and Different Forms of Adenylyl Cyclase," *Life Sciences*, 56(11/12):973–980 (1995) (Elsevier Science, Ltd., Editors).

Orlek, et al., "Design and Synthesis of Novel Muscarinic Agonists Containing the 1,2,4–Triazine Ring as an Ester Bioisostere," *Bioorgan. & Med. Chem. Letters*, 4(12):1411–1414 (1994).

Peralta, "Dual Modulation of a Potassium Channel by the M1 Muscarinic and B2–Adrenergic Receptors," *Life Sciences*, 56(11/12):957–964 (1995).

Qian, C.; et al., "Epibatidine is a nicotinic analgesic," *European J. Pharmacology*, 250(3):R–13–14 (1993).

Qian, et al., "Acetylcholine Muscarinic Receptor Regulations of the RAS/RAF/MAP Kinase Pathway," *Life Sciences*, 56(11/12):945–949 (1995).

Qian, et al., "Effects of Epibatidine on Body Weight in Mice," *Med. Chem. Res.*, 4:493–501 (1994).

Reavill, "Action of nicotine on dopamine pathways and implications for Parkinson's disease," *Nicotine Psychopharmacology*, (Wonnacott, et al., Editors, Oxford University Press, 9:307–340 (1990).

Rhodes and Thomas, "Nicotine Treatment in Ulcerative Colitis," *Drugs*, 49(2):157–160 (1995).

Russell, et al., "Theoretical Background and Clinical Use of Nicotine Chewing Gum," *National Institute on Drug Abuse Research Monograph Series* 110–130 (1985).

Sahley et al., "Antinociceptive Effects of Central and Systemic Administration of Nicotine in the Rat," *Psychopharmacology*, 65:279–283 (1979).

Sakamoto, T., et al., "A Facile Synthesis of Ethynyl–Substituted Six–Membered N–Heteroaromatic Compounds," *Synthesis*, pp. 312, (1983).

Sanberg et al., "Nicotine potentiates the effects of haloperidol in animals and in patients with Tourette syndrome," *Biomedicine and Pharmacotherapy*, 43:19–23 (1989).

Sauerberg, et al., "Muscarinic Agonists as Analgesics. Antinociceptive Activity Versus $M_1$ Activity: SAR of Alkylthio–TZTP's and Related 1,2,5–Thiadiazole Analogs," *Life Sciences*, 56(11/12):807–814 (1995) (Elsevier Science, Ltd., Editors).

Sawyer and Narayanan, "Deacylation of Alkyl Carbamates: Selective Deprotection of Secondary Amines," *Syn. Comm.*, 13:135–138 (1983).

Schwarz, et al., "Mutations of Aspartate 103 in the Hm2 Receptor and Alterations in Receptor Binding Properties of Muscarinic Agonists," *Life Sciences*, 56(11/12):923–929 (1995).

Sheppard, et al., "3–(2–(3–Pyridinyl)thiazolidin–4–oyl)–Indoles, a Novel Series of Platelet Activating Factor Antagonists," *J. Med. Chem.*, 37:2011–2032 (1994).

Showell, et al., "L–696,986: A Functionally Selective and Potent Muscarinic $M_1$ Receptor Partial Agonist," *Medicinal Chem. Res.*, 3:171–177 (1993).

Spande, et al., "Epibatidine: A Novel(Chloropyridyl) Azabycycloheptane with Potent Analgesic Activity from an Ecuadoran Poison Frog," *Org. Chem.* 5:332–335 (1992).

Spande, et al., "Epibatidine,: A Novel(Chloropyridyl) azabicycloheptane with Potent Analgesic Activity from an Ecuadoran Poison Frog," *J. Am. Chem. Soc.*, 114:3475–3478 (1992).

Steinbach and Ifune, "How many kinds of nicotinic acetylcholine receptor are there?" *Trends Neurosci.*, 12:3–6 (1989).

Stinson, S., "Osmium(III) Found to Disrupt Aromaticity," *Chemical and Engineering News*, pp. 27–30 (Nov. 1992).

Taylor, "Agents Acting at the Neuromuscular Junction and Autonomic Ganglia," *The Pharmacological Basis of Therapeutics*, (Goodman and Gilman, Editors, Pergamon Press, 9:166–186 (1990).

Thomsen, et al., "Preparation of B–Keto Sulfones from [(Phenylsulfonyl)methylene]dilithium and Acid Chlorides," *J. Org. Chem.*, 53:906–907 (1988).

Tobin et al., "Cigarette Smoking and Inflammatory Bowel Disease," *Gastroenterology*, 93:316–321 (1987).

Toube, T.P., "1.9 Cycloaddition Reactions of Acylpyrroles and Their Derivatives," *Pyrroles*, Part 2, (Jones, R. A., ed.) John Wiley, New York, pp. 92–95 (1992).

Tripathi et al., "Nicotine–Induced Antinociceptoin in Rats and Mice: Correlation with Nicotine Brain Levels," *J. Pharmacol. Exp. Ther.*, 221(1):91–96 (1982).

Trost, B.M., et al., "Desulfonylation of Aryl Alkyl Sulfones," *Tetrahedron Lett.*, pp. 3477–3478 (1976).

Tsukamoto, et al., "Synthesis and Structure–Activity Studies of a Series of Spirooxazodine–2,4–diones: 4–Oxa Analogues of the Muscarinic Agonist 2–Ethyl–8–methyl–2,8–iazaspiro[4.5]decane–1,3–dione," *J. Med. Chem.*, 36: 2292–2299 (1993).

Volle, *Pharmacology of Ganglionic Transmission*, Kharkevich, D.A., ed., Springer–Verlag, Berlin, pp. 281–312 (1980).

Wani, M.C., et al., "Plant Antitumor Agents. IX. The Total Synthesis of dl–Camptothecin," *J. Am. Chem. Soc.*, 94:3631–3632 (1972).

Ward, et al., "Functionally Selective $M_1$ Muscarinic Agonists. 3. Side Chains and Azacycles Contributing to Functional Muscarinic Selectivity among Pyrazinylazacyles," *J. Med. Chem.*, 38:3469–3481 (1995).

Wess, et al., "Muscarinic Acetylcholine Receptors: Structural Basis of Ligand Binding and G Protein Coupling," *Life Sciences*, 56(11/12):915–922 (1995) (Elsevier Science, Ltd., Editors).

Williams, et al., "Neuronal Nicotinic Acetylcholine Receptors," *Drug News & Perspectives* 7(4):205–223 (1994).

EPIBATIDINE AND DERIVATIVES THEREOF AS CHOLINERGIC RECEPTOR AGONISTS AND ANTAGONISTS

This application is a U.S. national filing under 35 U.S.C. 371 of PCT/US94/10121, filed in the U.S. Receiving Office of the Patent Cooperation Treaty on Sep. 9, 1994, which is a continuatin of U.S. patent application Ser. No. 08/119,697, filed Sep. 10, 1993, (now abandoned).

BACKGROUND OF THE INVENTION

The present invention is directed to methods of treatment utilizing pharmaceutical compositions comprising epibatidine and/or synthetic derivatives thereof, wherein the utility of the composition is based upon the fact that the active compounds have been found to be cholinergic receptor agonists.

Epibatidine has the following structure. Epibatidine was first isolated by Daly et al. from skins of the Ecuadoran poison frog, Epipedobates tricolor (Daly, et al., *J. Am. Chem Soc.*, 102:830 (1980)). Its structure was determined by mass spectroscopy, infrared spectroscopy, and nuclear magnetic resonance as exo-2(6-chloro-3-pyridyl)-7-azabicyclo [2.2.1]-heptane (1) (Spande, et al., *J. Am. Chem. Soc.*, 114:3475 (1992)). This alkaloid has been shown to be a potent analgesic with a nonopioid mechanism of action. The analgesic effect of epibatidine was approximately 200-times higher than morphine using the hot plate assay, and approximately 500-fold that of morphine in eliciting the Straub-tail response. The epibatidine-induced analgesia was not blocked by the opioid receptor antagonist naloxone. Furthermore, it has been determined that epibatidine had a negligible affinity for the opioid receptor (1/8000 times that of morphine). See, Spande, et al., *J. Am. Chem. Soc.*, 114:3475 (1992).

The invention described herein is based on the discovery that epibatidine is a natural alkaloid nicotinic cholinergic receptor agonist. Other natural alkaloids are nicotine, first isolated from leaves of tobacco in 1828, and lobeline, first isolated from Lobelia inflata (India tobacco) in 1915. See, Taylor, *Goodman and Gilman's The Pharmacological Basis of Therapeutics*, 18th Ed., Gilman et al., eds., Pergamon Press, pp. 166–186 (1990). Nicotine is both a ganglionic and skeletal muscle receptor agonist and has been found to exert a potent analgesia on thermal stimuli as measured by the hot-plate or tail-flick test in both rats and mice (Tripathi, et al., *J. Pharmacol. Exp. Therap.*, 221:91 (1982); Sahley et al., *Pschopharmacology*, 65:279 (1979); Colley, et al., *Pharmacol. Biochem. Behav.*, 36:413 (1990); Christensen, et al., *J. Neural. Transm. GenSec.*, 80:189 (1990)).

Differences in responses mediated by acetylcholine result from actual differences in cholinergic receptors. Responses evoked by acetylcholine are described as being nicotinic or muscarinic, which have led to the subclassification of cholinergic receptors as nicotinic cholinergic receptors or muscarinic cholinergic receptors. The response of most autonomic effector cells in peripheral visceral organs is typically muscarinic, whereas the response in parasympathetic and sympathetic ganglia, as well as responses of skeletal muscle, is nicotinic. The nicotinic receptors of autonomic ganglia and skeletal muscle are not homogeneous because they can be blocked by different antagonists. Thus, d-tubocurarine effectively blocks nicotinic responses in skeletal muscle, whereas hexamethonium and mecamylamine are more effective in blocking nicotinic responses in autonomic ganglia, thereby confirming heterogeneity in nicotinic cholinergic receptors (named $N_M$ and $N_N$ receptor respectively).

Muscarinic receptors may also be divided into at least two subtypes, $M_1$ and $M_2$. In general, muscarinic cholinergic receptors with the pharmacological profile characteristic of the $M_1$ subtype are found in autonomic ganglia and in the CNS, whereas $M_2$ muscarinic receptor exist at neuroeffector junctions of organs innervated by the parasympathetic system.

Nicotinic receptors are ligand-gated ion channels, and their activation always causes a rapid increase in cellular permeability to $Na^+$ and $K^+$, depolarization, and excitation. The primary structures of nicotinic receptors from various species have been deduced by molecular cloning. (Numa et al., *Cold Spring Harbor Symp. Ouant. Biol.*, 48: 57 (1983)). The nicotinic receptors are pentameric proteins that are composed of at least two distinct subunits. Each subunit contains multiple membrane-spanning regions, and the individual subunits surround an internal channel. One of the subunits (designated α) is present in at least two copies and forms the ligand binding site on the receptor.

Nicotinic receptors ($N_N$) in the CNS also exist as pentamers; they are composed of only two subunits, α and β. Further complexity arises because multiple forms of α and β have been detected (Steinbach and Ifune, *Trends Neurosci.*, 12: 3 (1989)). In general, each of the α and β subunits is found in discrete regions of the brain.

Drugs that stimulate cholinergic receptor sites on autonomic ganglia can be grouped into two major categories. The first group consists of drugs with nicotinic specificity, including nicotine itself. Their excitatory effects on ganglia are rapid in onset, are blocked by nondepolarizing ganglionic blocking agents, and mimic the initial excitatory postsynaptic potential (EPSP). The second group is composed of agents such as muscarine and methacholine. Their excitatory effects on ganglia are delayed in onset, blocked by atropine-like drugs, and mimic the slow EPSP.

Ganglionic blocking agents impair transmission by actions at the nicotinic receptors and also may be classified into two groups. The first group includes those drugs that initially stimulate the ganglia by an ACh-like action then block them because of a persistent depolarization (e.g., nicotine); prolonged application of nicotine results in desensitization of the cholinergic receptor site and continued blockade (Volle, in: *Pharmacology of Ganglionic Transmission*, Kharkevich, D.A., ed. Springer-Verlag, Berlin, pp. 281–312, 1980). The blockage of autonomic ganglia by the second group of blocking drugs, of which mexamethonium and trimethaphan can be regarded as prototypes, does not involve prior ganglionic stimulation or changes in the ganglionic potentials. These agents impair transmission either by competing with ACh for ganglionic cholinergic receptor sites or by blocking the channel when it is open; therefore, the initial EPSP is blocked and ganglionic transmission is inhibited.

Parkinsonism is a clinical syndrome comprised of four cardinal features: bradykinesia, muscular rigidity, resting tremor, and abnormalities of posture and gait. Despite advances in the understanding of the pathophysiology and the treatment of parkinsonism, its cause remains unknown. Classical investigations performed in the 1950's and 1960's clearly established the basal ganglia of the brain and specifically the nigrostriatal dopaminergic system as the site of the fundamental lesion in Parkinson's disease. Abundant evidence suggests that parkinsonism is a syndrome of deficiency in the dopaminergic innervation of the basal ganglia owing to degeneration of neurons in the substantia nigra (Ehringer and Hornykiewicz et al., *Klin. Wochenschr.*, 38: 1236 (1960)). Since dopamine does not cross the blood-brain barrier when administered systemically, it has no therapeutic effects in parkinsonism. However, levodopa, the immediate metabolic precursor of dopamine, is transported into the brain and permeates into striatal tissue, where it is decarboxylated to dopamine. Clinical studies demonstrated the value of replenishment of depleted stores of dopamine in parkinsonism.

Among the panoply of other neurotransmitters contained in the basal ganglia, acetylcholine is currently known to be of significance in the pharmacotherapy of parkinsonism. A simplistic, but useful, neurochemical model of the function of the basal ganglia suggests that the neostriatum (caudate nucleus and putamen) normally contains balanced inhibitory dopaminergic and excitatory cholinergic components (*Duvoisin. Arch. Neurol.*, 17: 124 (1967)). Although cholinergic neurons are not damaged in Parkinson's disease, the decrease in dopaminergic activity results in a relative excess of cholinergic influence. Consequently, a second strategy for the treatment of parkinsonism is to block cholinergic activity in an attempt to restore the balance of dopaminergic and cholinergic tone in the striatum. Furthermore, dopaminergic agonists and cholinergic (muscarinic) antagonists are often combined effectively.

Many epidemiology reports have found that smokers are less likely to develop Parkinson's disease than non-smokers. Evidence supporting a possible protective role for nicotine include the findings of Janson et al., *Acta Physisologica Scandinavica*, 132: 589 (1988) that pretreatment with nicotine will prevent some of the damage to the extra-pyramidal system by the illicit drug MPTP which produces a Parkinson-like syndrome in human.

Another movement disorder, Tourette's syndrome, seems to be responsive to nicotine (Devor and Isenberg, *Lancet*, 2: 1046 (1989)). Sanberg et al., *Biomedicine and Pharmacotherapy*, 43: 19 (1989) and Moss et al., *Life Sciences*, 44: 1521 (1989) found that nicotine potentiated the therapeutic effects of haloperidol in patients with Tourette's syndrome. They also found that nicotine would potentiate haloperidol-induced hypokinesia in rats.

The mechanism of action of nicotine in movement disorder is unknown. Development of tolerance to nicotine was found in humans. It was reported that tachyphylaxis developed to nicotine-induced antinociception in rats (1.25 mg/kg, s.c.) within 10 minutes lasted for up to 14 hours; but tachyphylaxis did not develop to nicotine-induced antinociception in mice (3 mg/kg, s.c.). (Tripathi, et al., *J. Pharmacol. Exp. Ther.*, 22: 91 (1982)). Since the antinociception of nicotine is mediated through central nicotinic receptors, the mechanism of nicotine-induced desensitization of ganglionic nicotinic receptors may explain the development of tachyphylaxis to central nicotine. Nicotine initially stimulates the ganglia by an ACh-like action, as indicated by a transient tremor, then blocks them because of a persistent depolarization (Volle, in: *Pharmacoloy of Ganglionic Transmission*, Kharkevich, D. A., ed., Springer-Verlag, Berlin, pp. 281–312, 1980). Furthermore, one can apply the same mechanism to elucidate the therapeutic effects of nicotine in movement disorders. Smoking or exposure to nicotine induces a persistent depolarization of cholinergic neurons in striatum, which markedly lessens or induces the loss of the response to the ACh transmitter, leading to a blockage of cholinergic activity. In addition, a large number of observations indicate that nicotine can enhance dopamine release via nicotinic cholinergic receptors located on the dopaminergic nerve is terminals. This change is correlated with an increase in the fluorescence intensity of dopamine within the zona compacta of the substantia nigra (Lichtensteiger, et al., *Brain Res.*, 117, 85, (1976)). Nicotine, continuously administered via subcutaneously implanted minipumps, can exert protective effects on the nigrostriatal dopaminergic neurons as an increased number of dopaminergic nerve cell bodies seemed to survive. It has been hypothesized that these protective effects of nicotine are due to a desensitization of the nicotinic cholinergic receptors on the dopamine neurons, leading to a reduced firing rate, improved ionic homeostasis and thus to reduced energy demands (Janson, et al., *Act. Physiol. Scand.*, 132: 589 (1988); Reavill, in *Nicotine Psychopharmacoloy*, Wonnacott, et al., eds., Oxford University Press, pp. 307 (1990)). A putative anti-Parkinsonian action of nicotine and smoking may be due at least in part to a release action of nicotine on dopaminergic nerve terminals.

The therapeutic effects of nicotine in Parkinson's disease were found more than half century ago (Moll, *Brit. Med. J.*, 1: 1079 (1926)). Besides parkinsonism, nicotine was employed as a potential drug in the treatment of Tourette's Syndrome (another movement disease) (McConville et al., *Am. J. Psychiatry*, 148: 739 (1991)), ulcerative colitis (Jick et al., *N. Engl. J. Med.*, 308: 261 (1983); Tobin et al., *Gastroenterology*, 93: 316 (1987), Lashner et al., *Digest. Dis. Sci.*, 35: 827 (1990), aphthous ulcers (Bittoun, *Med. J. Australia*, 164: 471 (1991)), smoking cessation (Glassman and Covey, *Drugs*, 40: 1 (1990); Gourlay and McNeil, *Med, J. Australia*, 153: 699 (1990)), and body weight loss/gain (Grunberg et al., *Psychopharmocology*, 83: 93 (1984)). The therapeutic effects of nicotine were reviewed by Jarvik (*Brit. J. Addict.*, 86: 571 (1991)). Agonists and antagonists of nicotine useful as smoking deterrents are reported in U.S. Pat. No. 4,966,916 (Abood, 1990). Nicotine has not generally been used as a clinical drug, particularly due to its toxicity and its low potency in the treatment of disease states including parkinsonism and other movement disorders.

Development of drugs that provide a more selective, more potent or more persistent depolarization of cholinergic neurons in the CNS than nicotine will provide a new method for the treatment of Parkinson's disease and other movement disorders.

Therefore, it is an object of this invention to provide new compounds that are cholinergic receptor ligands.

It is still another object of the present invention to provide compounds which are agonists and antagonists of muscarinic and nicotinic receptors.

It is still another object of the present invention to provide new methods for the treatment of pain.

It is another object of the present invention to provide compositions and methods for the treatment of cognitive, neurological, and mental disorders, as well as other disorders characterized by decreased or increased cholinergic function.

It is yet another object of the present invention to provide pharmaceutical compositions and new methods of treatment which of certain disease states or conditions, including movement disorders such as Parkinson's disease, Tourette's syndrome, and the like, Alzheimer's disease, ulcerative colitis and aphthous ulcer, and for other medical uses, including smoking cessation and body weight loss.

SUMMARY OF THE INVENTION

It has been discovered that epibatidine and synthetic analogs thereof are cholinergic receptor ligands, and therefore, can be used to treat medical conditions characterized by decreased or increased cholinergic function, and in particular, which can be treated by nicotinic or muscarinic agonists or antagonists. The compounds can be used in the treatment of cognitive, neurological, and mental disorders, as well as other disorders characterized by decreased or increased cholinergic function.

The selectivity of the selected compound for various receptor subtypes is easily determined by routine in vitro and in vivo pharmacological assays known to those skilled in the art, and described in more detail below. The receptor subtype selectivity is expected to vary based on the substituents on the 7-aza-norbornane or norbornene ring.

The synthetic analogs of epibatidine include those of the structure:

where:

$R^1$ and $R^4$ are independently selected from the group consisting of hydrogen, alkyl, including —$CH_3$; alkylhydroxy, including —$CH_2OH$; alkyloxyalkyl, including —$CH_2OCH_3$; alkylthioalkyl, including —$CH_2SCH_3$; alkylamino, including —$CH_2NHCH_3$ and —$CH_2N(CH_3)_2$; oxyalkyl, including —$OCH_3$; carboalkoxy, including carbomethoxy; alkyl; aryl; heteroaryl such as pyridine or substitutes of pyridine, thioalkyl, including —$SCH_3$, and Q (defined below);

each $R^3$, $R^5$ and $R^6$ may be independently selected from the group consisting of hydrogen, alkyl, including —$CH_3$; alkylhydroxy, including —$CH_2OH$; alkyloxyalkyl, including —$CH_2OCH_3$; alkylthioalkyl, including —$CH_2SCH_3$; alkylamino, including —$CH_2NH_2$; alkylaminoalkyl or alkylaminodialkyl, including —$CH_2NHCH_3$ and —$CH_2N(CH_3)_2$; oxyalkyl, including —$OCH_3$; thioalkyl, including —$SCH_3$; halo, including —Cl; —$CF_3$; —$NH_2$; alkylamino or dialkylamino, including —$N(CH_3)_2$ and —$NHCH_3$; —$CO_2H$; —$CO_2$-alkyl, including —$CO_2CH_3$; —C(O)-alkyl,. including —$C(O)CH_3$; —CH; —$C(O)NH_2$; —C(O)NH(alkyl); —C(O)N(alkyl)$_2$, including —$C(O)N(CH_3)_2$; alkyl; and —$SO_n$(alkyl), —$SO_n$(aryl), —$SO_n$(heteroaryl), wherein n=0, 1 or 2;

$R^5$ and $R^6$ together can be alkylidene or haloalkylidene, including —$CH_2$— and —$CF_2$—;

each $R^2$ may be independently selected from the group consisting of hydrogen, alkyl, including —$CH_3$; —$CH_2$—; HC=$CH_2$; alkylhydroxy, including —$CH_2$—OH; alkyloxyalkyl, including —$CH_2O$—

(alkyl); alkylamine, including —$CH_2NH_2$; carboxylate, —CH; —Q; —C(O)Q; and —alkyl(Q); wherein Q is selected from the group consisting of:

and wherein the Q moiety can be optionally substituted with from 1 to 3 substituent groups W;

wherein each substituent group W is selected from the group consisting of alkyl, including —$CH_3$; is halo, including —Cl, —Br and —F; aryl; heteroaryl; —OH; oxyalkyl, including —$OCH_3$; —SH; thioalkyl, including —$SCH_3$; —SO(alkyl), including —$SOCH_3$; —$SO_2$alkyl, including —$SO_2CH_3$; —$OCH_2CH=CH_2$; —$OCH_2(C_6H_5)$; —$CF_3$; —CN; alkylenedioxy, including methylenedioxy; —$CO_2H$; —$CO_2$alkyl, including —$CO_2CH_3$; —$OCH_2CH_2OH$; —$NO_2$; —$NH_2$; —NH(alkyl), including —$NHCH_3$; —N(alkyl)$_2$, including —N($CH_3)_2$; —NCH(O)alkyl, including —$NHC(O)CH_3$; —$SO_2CF_3$; and —$NHCH_2$aryl, including —$NHCH_2(C_6H_5)$;

$R^7$ is selected from the group consisting of hydrogen; alkyl, including —$CH_3$; —$CH_2$—(cycloalkyl), including —$CH_2$—(cyclopropyl); —$CH_2CH=CH_2$; —$CH_2CH_2(C_6H_5)$; alkylhydroxy, including —$CH_2CH_2OH$; alkylamino(alkyl)$_{0-2}$, including —$CH_2CH_2N(CH_3)_2$; alkoxyalkyl; alkylthioalkyl; and aryl; and wherein the lines—represent optional double bonds in the formula.

The term alkyl, as used herein, refers to a $C_1$ to $C_{30}$, preferably a $C_1$ to $C_{20}$, straight or branched group. Lower alkyl means a $C_1$ to $C_2$, preferably a $C_1$ to $C_6$ group. Typical $C_1$–$C_6$ alkyl groups include methyl, ethyl, n-propyl, i-propyl, n-butyl, t-butyl, pentyl and hexyl groups.

Cycloalkyl means a $C_3$ to $C_{12}$, preferably a $C_3$ to $C_8$ cyclic group. Typical C cycloalkyl groups include cyclopropyl, cyclobutyl, cyclopentyl, cyclohexyl, cycloheptyl, and cyclooctyl groups.

Typical $C_2$–$C_6$ carboxylic acyl groups include acetyl, propanoyl, i-propanoyl, butanoyl, s-butanoyl, pentanoyl and hexanoyl groups.

Typical aryl groups include phenyl, naphthyl, phenanthryl, anthracyl and fluorene groups.

Typical aryl-substituted carboxylic acid groups include the above-mentioned carboxylic acyl groups substituted by one or more aryl groups, e.g., diphenylacetoxy and fluorenecarboxy groups.

Typical alkaryl groups include the above-listed aryl groups substituted by one or more $C_1$–$C_6$ alkyl groups.

Typical aralkyl groups include a $C_1$–$C_6$ alkyl group substituted by one of the above-listed aryl groups, e.g., phenethyl, phenylpropyl, phenylbutyl, phenylpentyl and phenylhexyl groups as well as the branched chain isomers thereof.

Typical $C_1$–$C_6$ alkoxycarbonyl groups include carbonyl substituted by methoxy, ethoxy, propanoxy, i-propanoxy, n-butanoxy, t-butanoxy, i-butanoxy, pentanoxy, and hexanoxy groups.

Typical aralkyl groups include the above-listed $C_1$–$C_6$ alkyl groups substituted by phenyl, naphthyl, phenanthryl, and anthracyl groups.

Typical $C_2$–$C_6$ alkenyl groups include vinyl, alkyl, 2-butenyl, 2-pentenyl, and 2-hexenyl groups.

Typical $C_2$–$C_6$ alkynyl groups include acetynyl and propargyl groups.

Typical halo groups include fluorine, chlorine, bromine and iodine.

Typical aroyl groups include carbonyl substituted by phenyl, naphthyl, phenanthryl, and anthracyl groups.

Typical aralkanoyl groups include carbonyl substituted by the above-listed aralkyl groups.

Typical aralkoxy groups include the above-listed $C_1$–$C_6$ alkoxy groups substituted by phenyl, naphthyl, phenanthryl, and anthracyl groups.

Typical substituted aryl groups include the above-listed aryl groups substituted by halo, hydroxy, $C_1$–$C_6$, alkoxy, amino and the like.

Typical heteroaryl groups include furyl,. thienyl, pyrrolyl, thiazolyl, pyridyl, pyrimidinyl, pyrizinyl, oxazolyl and phthalimido groups which may be fused to a benzene ring.

Typical substituted heteroaryl groups include the above-listed heteroaryl groups substituted by halo, $C_1$–$C_6$ alkyl and the like.

Typical $C_5$–$C_6$ heterocycloalkyl groups include tetrahydrofuranyl, tetrahydropyranyl, piperidinyl, piperazinyl, morpholino and pyrrolidinyl groups.

Additional substituent groups for the above include halogen, hydroxy, $CF_3$, $C_1$–$C_6$ acyl, $C_1$–$C_6$ alkyl, $C_2$–$C_6$ alkenyl, $C_2$–$C_6$ alkynyl, $C_1$–$C_6$ alkoxy, $C_6$–$C_{18}$ aryl, $C_2$–$C_6$ dialkoxymethyl, cyano, $C_3$–$C_6$ cycloalkyl, $C_3$–$C_6$ heterocycloalkyl, $C_3$–$C_{15}$ dialkylaminoalkyl, carboxy, $C_2$–$C_6$ carboxylic acid, carboxamido, $C_1$–$C_6$ haloalkyl, $C_1$–$C_6$ haloalkylthio, alkyl, $C_7$–$C_{20}$ aralkyl, a $C_3$–$C_6$ heterocycloalkyl ring fused to a benzene ring, $C_1$–$C_6$ alkylthio, $C_1$–$C_6$ alkyl-sulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro $C_2$–$C_{15}$ dialkylsulfamoyl, and the like.

The present invention will be appreciated more completely by those having ordinary skill in this art upon consideration of the detailed description of the invention, which is provided below.

DETAILED DESCRIPTION OF THE PREFERRED EMBODIMENTS

As described above, the present invention is directed to a method for treating disorders characterized by an increase or decrease in cholinergic activity that includes the administration of an effective amount of epibatidine or a derivative thereof, as set out above. These compounds are useful for the a wide variety of mental or cognitive disorders, including Parkinson's disease, Tourette's Syndrome, Alzheimer's disease, as well as other medical conditions such as ulcerative colitis, aphthous ulcer, cessation of smoking and body weight loss.

It has been discovered that:

1. Epibatidine at approximately 1/100th the dose of nicotine (<10 μg/kg) mimicked nicotine-induced analgesia, hyperventilation, and tremor; with somewhat larger doses (>20 μg/kg), the tremor is followed by convulsion and death results from failure of respiration. Since the analgesic dose of nicotine is 10–50 times higher than its therapeutic dose (Reavill, in *Nicotine Psychopharmacology*, Wonnacott, et al., eds., Oxford University Press, pp. 307, (1990)), the satisfactory therapeutic effects may be achieved by the very potent nicotinic receptor agonist epibatidine at hundreds of nanograms to a few micrograms per kg. In this low dose range, epibatidine may not induce the undesired CNS effects that nicotine induces. When a higher dose of epibatidine is needed, these CNS responses to epibatidine could be avoided by a low starting dose, followed by a high dose a few minutes after the first dose.

2. The pretreatment with mecamylamine (a central non-depolarizing nicotinic blocker) at a very low dose completely blocked epibatidine-induced analgesia and other CNS responses.

3. The opioid antagonist naloxone and the α-2 adrenoceptor antagonist yohimbine blocked nicotine-induced analgesia (Tripathi et al., *J. Pharmacol. Exp. Ther.*, 221: 91 (1982)), but did not antagonize epibatidine-induced analgesia.

4. Tachyphylaxis developed to epibatidine was much higher and longer than that developed to nicotine in both rats and mice.

I. Pharmaceutical Compositions

The pharmaceutical composition of the present invention may be administered to any host animal (for example, humans, equines, canines, bovines and other animals, and in particular, mammals) in need of treatment, by any suitable route including oral, rectal, nasal, topical (including buccal and sublingual), vaginal and parenteral (including, transdermal, subcutaneous, intramuscular, intravenous and intradermal). It will be appreciated that the preferred route will vary with the condition and age of the recipient, the nature of the condition and the active ingredients. The host animal includes In general a suitable dose for each of the above-mentioned conditions (e.g., Parkinson's disease, Tourette's syndrome, etc.) will be in the range of from about 0.1 to 20 μg per kilogram body weight of the recipient (e.g., a human) per day, preferably in the range of from about 0.5 to 2 μg per kilogram body weight per day and most preferably in the range of from about 1 to 2 μg per kilogram body weight per day. The desired dose is preferably presented as two, three, four, five, six or more sub-doses administered at appropriate time intervals throughout the day. These sub-doses may be administered in unit dosage form, for example, containing from about 0.05 to 5 μg, preferably from about 0.25 to 1.5 μg, and most preferably from about 0.5 to 1 μg of active ingredient per unit dosage form.

Ideally, the active ingredient should be administered to achieve peak plasma concentrations of the active ingredient of from about 0.2 to 30 ng/ml, preferably from about 1 to 15 ng/ml, most preferably about 2 to 10 ng/ml. This may be achieved, for example, by the intravenous injection of a 0.1 to 5% solution of the active ingredient, optionally in saline, or orally administered as a bolus containing about 0.2 to 50 μg/kg of the active ingredient. Desirable blood levels may be maintained by continuous infusion to provide about 0.005 to 2 μg/kg/hour or by intermittent infusions containing about 0.1 to 5 μg/kg of the active ingredient.

While it is possible for the active ingredient to be administered alone, it is preferable to present it as a pharmaceutical formulation. The formulations of the present invention comprise the active ingredient, as defined above, together with at least one pharmaceutically acceptable carrier, diluent or excipient. Preferred formulations include those adapted for oral, rectal, nasal, topical (including buccal and sublingual), vaginal or parenteral (including subcutaneous, intramuscular, intravenous and intradermal) administration. The formulations may conveniently be presented in unit dosage form and may be prepared by methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations of the present invention adapted for oral administration may be presented as discrete units such as capsules or tablets each containing a predetermined amount of the active ingredient; as a powder or granules; as a solution or a suspension in an aqueous or non-aqueous liquid; or as an oil-in-water liquid emulsion or a water-in-oil liquid emulsion.

The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked providone, cross-linked sodium carboxymethyl cellulose) surface-active or dispersing agent.

Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl-methyl cellulose in varying proportions to provide the desired release profile. Tablets may optionally be provided with an enteric coating, to provide release in parts of the gut other than the stomach.

Formulation adapted for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations adapted for rectal administration may be presented as a suppository with a suitable base comprising for example cocoa butter or salicylate.

Formulations adapted for vaginal administration may by presented as pessaries, tampons, creams, gels, pasted, foams or spray formulations containing in addition to the active ingredient such carriers as are known in the art to be appropriate.

Formulations adapted for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be present in unit-dose or multi-dose sealed containers, for example, ampules and vials, and any be stored in a freeze-dried (lyophilized) condition requiring only the addition of the sterile liquid carrier, for example water for injections, immediately, prior to use. Extemporaneous injection solutions and suspensions any be prepared from sterile powders, granules and tablets of the kind previously described.

Preferred unit dosage formulations as those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

II. Evaluation of Biological Activity of Active Compounds

Methods for the determination of the specific cholinergic receptor activity profile for a selected compound is easily determined using known assays. For example, to determine which type or types of acetylcholinergic receptors a compound is interacting with, in vitro competitive binding assays can be performed using specific radioligands. A compound's ability to compete with a specific radioligand for receptor binding indicates an affinity for that receptor type. Radiolabelled nicotine (or cytisine) and quinuclidinyl benzilate are commonly used for nicotine and muscarinic receptor types, respectively. However, whether or not the compound is an agonist or antagonist is typically not determined by these assays.

To differentiate between agonists or antagonists, cell, tissue or animal-based in vitro or in vivo assays are typically employed. For nicotinic receptor ligands, one assay involves treating an animal with compound, then measuring a pharmacological activity associated with nicotinic receptor agonism, such tail-flick analgesia. If compound treatment resulted in analgesic activity, the compound is considered a nicotinic agonist. The compound's agonist activity should also be blocked by known nicotinic receptor antagonists. A similar protocol can be utilized if a cell-based assay, such as release of dopamine from striatal synaptosomes, is used.

If there is no nicotinic agonist activity, e.g. analgesia, in this example, after compound treatment, an effective dose of a known nicotinic agonist (such as nicotine) is subsequently given to the compound-treated animal. If the compound is an antagonist with the ability to block the effects of a known agonist, then the resulting analgesic activity would be less than that expected for the given dose of agonist.

Muscarinic agonists/antagonists can be characterized using appropriate muscarinic receptor-mediated in vitro and in vivo assays. Pharmacologic approaches can include, for example, include receptor-mediated mobilization of $Ca^{+2}$ in cultured cells, depolarization of the rate superior cervical ganglion, or contraction of the longitudinal muscle myenteric-plexus preparation of the guinea pig.

Compounds which act as nicotinic receptor agonists are useful in the treatment of cognitive neurological and mental disorders, including Parkinson's disease, Tourette's Syndrome, Alzheimer's disease, attention deficit disorder, dementia, multi-infart dementia, vascular dementia, cognitive impairment due to organic brain disease including due to alcoholism and brain diseases, general problems with information processing, deficient regional cerebral blood flow and cerebral glucose utilization, psychiatric disorders (e.g., schizophrenia and depression), as well as other conditions such as analgesia, ulcerative colitis, aphthous ulcer, cessation of smoking, body weight loss and treatment of the symptoms of anxiety and frustration associated with withdrawal from other addictive substances, such as, cocaine, diazepam or alcohol. Nicotinic receptor agonists can also be used for veterinary purposes, including as respiratory stimulants, ectoparasiticides, and anthelmitics.

Compounds which act as nicotinic receptor antagonists are useful as ganglion-blocking agents, in the control of blood pressure in hypertension, in autonomic hyperreflexia regulation, in the control of hypotension during surgery and in the reduction of bleeding during operations. These compounds can also be used as stabilizing neuromuscular blocking agents which are extensively used as adjuvants in anesthesia for the relaxation of skeletal muscles, treatment for severe muscle spasms and ventilatory failure from various causes such as obstructive airway disorders. In addition, nicotinic receptor antagonists are useful as depolarizing neuromuscular blocking agents, for example, as skeletal muscle relaxants in endotracheal intubation or psychiatric electroshock therapy to prevent muscle and bone damage. Nicotine antagonists are also useful in blocking both the secretagogue and mitogenic effects of nicotine on cancer cells such as human small cell lung carcinoma. Finally, nicotine antagonists can be used as antidotes for curare/nicotine poisoning.

Muscarinic receptor agonists are widely used for ophthalmic purposes, for example, in the treatment of glaucoma to reduce intraocular pressure, applied alone or in combination with β-adrenergic blocking drugs or sympathomimetic agents, or for the treatment of accommodative esotropia. These agonists are also useful for one or more of the following indications: breaking adhesions between the iris and the lens; for the treatment of various disorders involving the depression of smooth muscle activity without obstruction (postoperative atony, congenital megacolon); in stimulating smooth muscle activity in the urinary and gastrointestinal tract; in reflux esophagitis, in the treatment of postoperative atonia of the stomach or bowel; for gastric retention following bilateral vagotomy; for congenital megacolon and combating esophageal reflux; in the treatment of urinary retention and inadequate emptying of the bladder postoperatively or post partum; and in the treatment of memory disorders and cognitive functions of Alzheimer's patients. The efficacy and side-effects of uscarinic receptors may be improved by optimizing their differential activity on various muscarinic receptor subtypes, e.g., M1 vs. M2/M3 receptors, as described by Showell, G. A., et al., *Medicinal Chemical Research*, 1993, 3:171–177.

Muscarinic receptor antagonists (antimuscarinic agents) are widely used in ophthalmology to produce mydriasis and/or cycloplegia. Selective M1 receptor antagonists are effective in treating peptic ulcer disease, and in the inhibition of gastric acid secretion. Antimuscarinic agents are also useful in treating increased tone or motility of the gastrointestinal tract, such as diarrheas, and in combating biliary and renal colics frequently in combination with an analgesic drug. Antimuscarinic agents, including quaternary ammonium compounds, are useful in treating obstructive pulmonary diseases such as chronic bronchitis or bronchial asthma. Cardioselective antimuscarinic agents are useful in treating symptomatic sinus bradycardia, e.g., in acute myocardial infarction, higher degree heart block and certain types of ventricular arrhythmias. Muscarinic receptor antagonists are also used in preoperative medication to counteract the vagal effects, to reduce excessive bronchial secretion, and to produce some sedation and amnesia. Centrally acting antimuscarinic agents are useful in the treatment of Parkinson's disease, by restoring the normal balance of cholinergic and dopaminergic neurotransmission in the basal ganglia, in the prevention of motion sickness, as a sedative, to relieve the symptoms of myasthenia gravis, in the antagonism of skeletal muscle relaxant effects of neuromuscular blocking agents, and in the treatment of poisoning by cholinesterase inhibitors such as those used in insecticides and chemical warfare. Such compounds are also useful to counteract anaesthesia effects, and in mushroom poisoning.

The clinical efficacy and safety of muscarinic receptor antagonists can be optimized by adjusting tissue selectivity, receptor subtype specificity and a balance of antagonism and agonism vs. different receptor subtypes, as well as by selective local (topical, aerosol, eye drop) or systemic administration of the drug.

The present invention will be further illustrated with reference to the following examples which will aid in the understanding of the present invention, but which are not to be construed as limitations thereof. All percentages report herein, unless otherwise specified, are percent by weight. All temperatures are expressed in degrees Celsius.

EXAMPLES

Animals:

Female and male CD-1 mice (20–25 g) and male CD-1 rats (300–400 g) were obtained from Charles River Labs (Wilmington, Mass.). Rats were housed in groups of two and mice were housed in group of five. All animals had free access to tap water and chow pellets in a thermostatically-controlled room temperature (20° C.) on a 12 hour light/dark cycle.

Antinociceptive Activity of Epibatidine and Derivatives:

After the control values were measured, the antinociceptive activity of various epibatidine isomers and derivatives (n=5/group) was tested 5 minutes after s.c. injection.

The antinociceptive activity of epibatidine isomers and derivatives is summarized in Table 1. The d,l- (CMI-545), d- (CMI-488) and l-epibatidine (CMI-477) all showed very high potency with $ED_{50}$ values of 10, 7 and 9 μg/kg, respectively.

Duration of Epibatidine- or Nicotine Induced Antinociception:

Duration of l-epibatidine- or nicotine-induced antinociception was assessed in mice by measuring antinociception at 2, 5, 10, 20 minutes after l-epibatidine (20 μg/kg, s.c.) or nicotine (5 mg/kg, s.c.).

Figure 1:
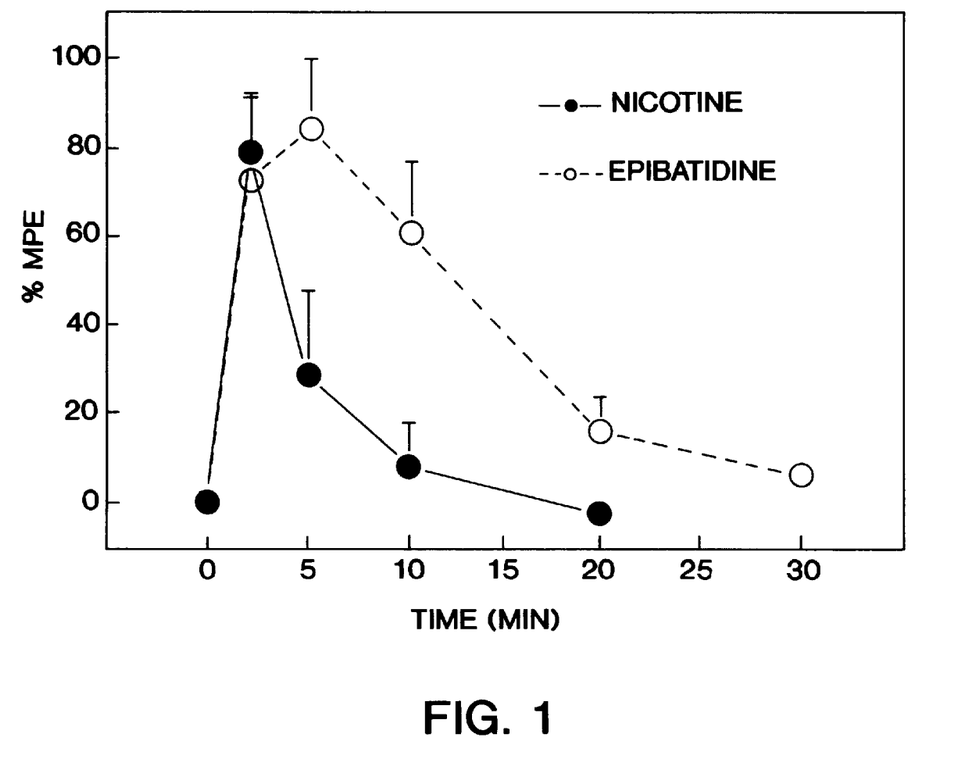
FIG. 1 is a graph of the time course for antinociception of l-epibatidine and nicotine in a tail-flick test. Note that the epibatidine duration is about twice that of nicotine.

As illustrated in FIG. 1, nicotine (5 mg/kg) and l-epibatidine (20 μg/kg) produced a decrease in responsiveness to radiant heat in the tail-flick test. A Friedman's analysis of variance test 15 revealed that the drug effect was significant (p<0.05). The onset of action was rapid with maximum antinociception occurring with 2 minutes for nicotine and 5 minutes for l-epibatidine. The duration of antinociception for l-epibatidine was about 20–30 minutes and for nicotine, 10 to 20 minutes.

Antagonixm of Epibatidine Antinociception in Mice:

Mide (n=7/group) were pretreated i.v. with either 0.9% saline or one antagonist (mecamylamine, hexamethonium, atropine, naloxone or yohimbine) 10 minutes before administration of l-epibatidine or nicotine at different doses. A control response (1.5–4 sec.) was determined for each animal before treatment and test latencies were assessed at 5 minutes after f-epibatidine administration (s.c., 5 ml/kg) or 2 minutes after nicotine (s.c., 5 ml/kg). The $ED_{50}$ values were calculated using the PC software, GraphPad InPlot (ver 3.0).

Various drugs were tested for antagonism of epibatidine at a high dose (20 μg/kg) and the resorts are contained in Table 2. l-Epibatidine-induced antinociception, as measured by the tail-flick test, was completely blocked by pretreatment with the centrally active nicotinic receptor blocker mecamylamine at a low dose (1 mg/kg), but was not significantly affected by the opiate receptor antagonist naloxone up to 3 mg/kg. The quaternary nicotinic receptor blocker hexamethonium (3 mg/kg), which passes only poorly into the central nervous system (Taylor, in *Goodman and Gilman's The Pharmacological Basis of Therapeutics*, 18th Ed., Gilman et al. Eds., Pergamon Press, pp 166–186 (1990)) 1957), showed less potent antagonism of l-epibatidine than did the corresponding tertiary antagonist mecamylamine. Yohimbine (an $\alpha_2$ adrenergic antagonist) was less is effective, and atropine (M receptor antagonism) was inactive in antagonizing l-epibatidine antinociception.

Figure 2A:
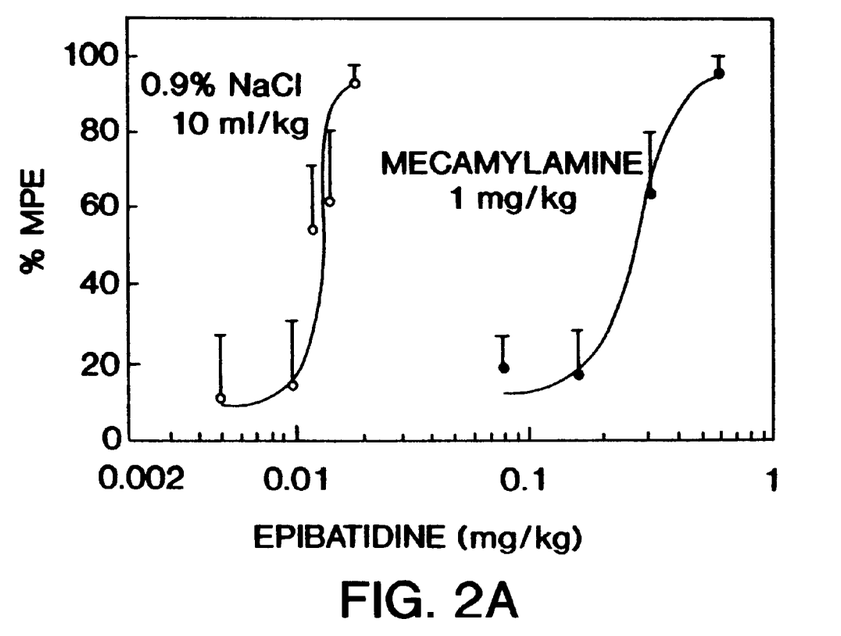
FIGS. 2A and 2B are graphs of the dose-response of antinociception induced by l-epibatidine (A) and nicotine (B). Note that l-epibatidine is about 200 times more potent than nicotine and that both antinociception activities were antagonized by the nicotinic receptor antagonist mecamylamine.
Figure 2B:
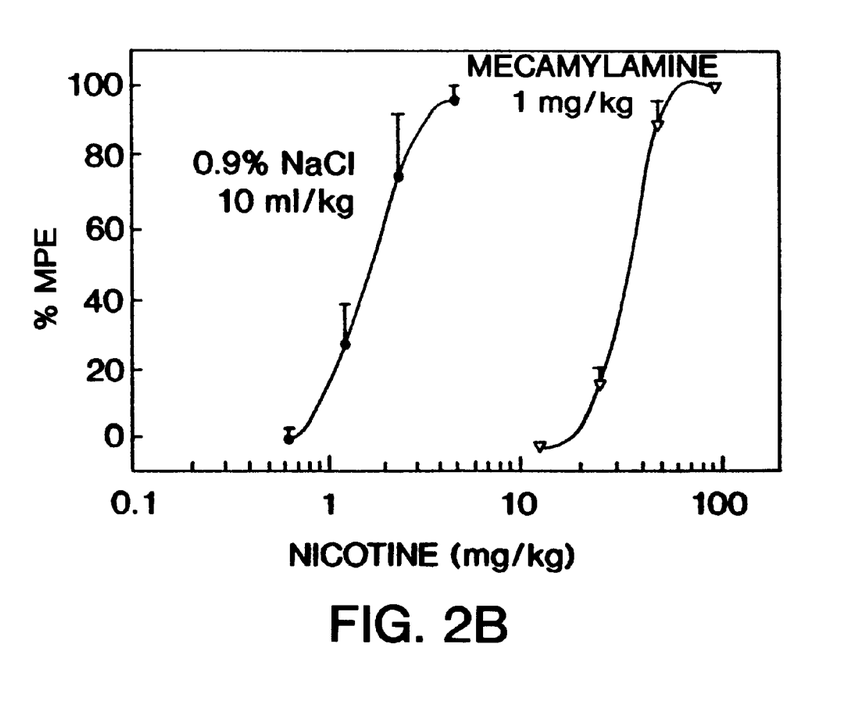

A dose-response relationship was established in mice for both nicotine (FIG. 3A) and l-epibatidine (FIG. 3B) by measuring antinociception at the time of maximal effects. Two minutes after nicotine administration (s.c.), the $ED_{50}$ value was found to be 1.4 mg/kg, whereas 5 minutes after l-epibatidine administration (s.c.) the $ED_{50}$ value was determined to be 13.6 μg/kg. A dose of nicotine or epibatidine as high as the $ED_{50}$ value produces tremors and sedation in most animals; with much higher doses (nicotine≧5 mg/kg, epibatidine≧20 μg/kg) tremors were followed by convulsions and death in some animals within 10 minutes after injection. Furthermore, in the animals pretreated with mecamylamine (1 mg/kg, i.v.) the dose response for either f-epibatidine or nicotine was measured. The potency ratio (i.e., ED50 value with blocker/ED50 value without blocker) for l-epibatidine and nicotine was found to be as high as 21.5 and 24.6, respectively (FIG. 2).

Figure 3:
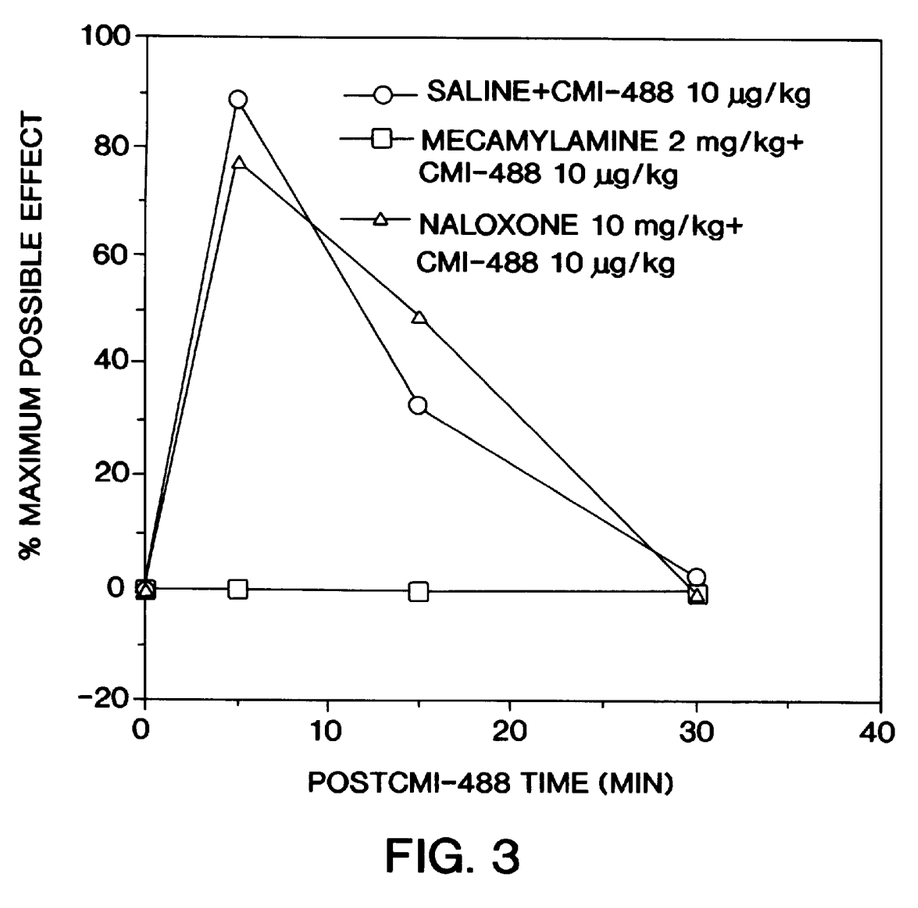
FIG. 3 is a graph of the time after administration of CMI-488 versus the percent possible effect of antinociception. The graph indicates that the antinociception of d-epibatidine is completely abolished by the nicotinic receptor antagonist mecamylamine, but it was not affected by the opiate receptor antagonist naloxone.
Figure 4A:
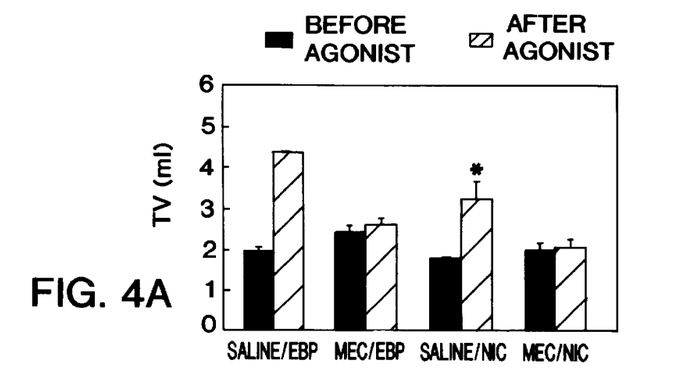
FIGS. 4A to 4D are a series of bar chart graphs indicating the effect of nicotine and l-epibatidine on tidal volume ($V_T$) respiratory frequency (RF), mean blood pressure (MBP), and heart rate (HR) in rats, and the blockage thereof by administration of the nicotinic receptor antagonist, mecamylamine. The asterisks indicate the level of significant difference from the values before nicotine (Nic) or l-epibatidine (EPB) administration (*$P<0.05$; **$P<0.01$).
Figure 4B:
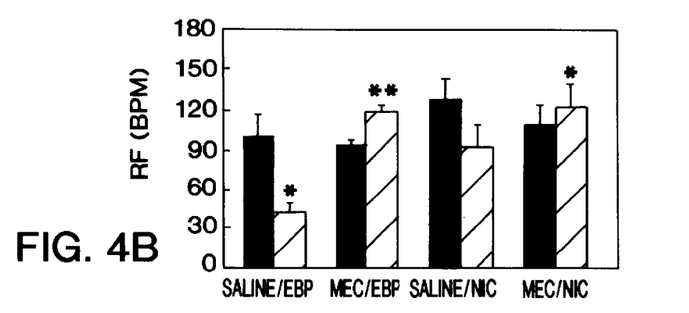
Figure 4C:
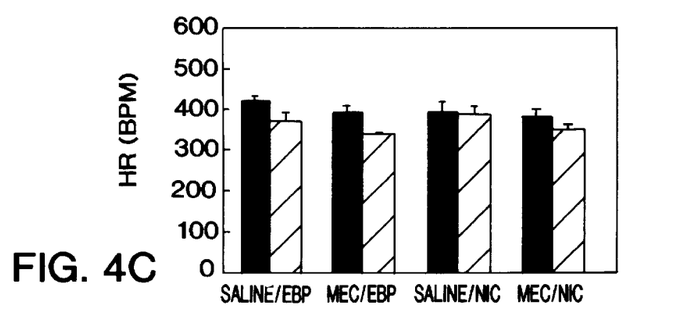
Figure 4D:
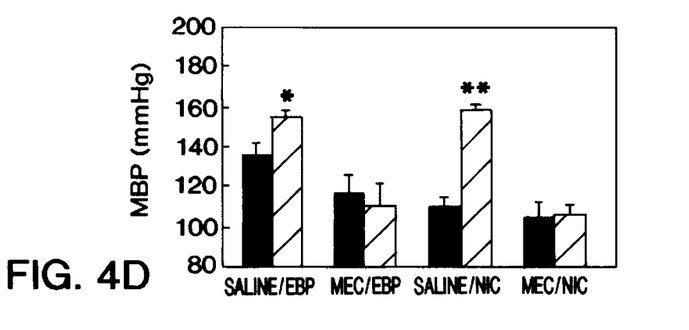

Also, the antinociception of d-epibatidine was completely abolished by the nicotinic receptor antagonist mecamylamine; but it was not affected by the opioid receptor antagonist naloxone (FIG. 3).

Effects of l-epibatidine and Nicotine on Respiration and Blood Pressure in Rats, and the Blockage Thereof by Mecamylamine:

Rats were anesthetized by sodium pentobarbital (50 mg/kg, i.p.) and body temperature of the animals was maintained by a Harvard homeothermic blanket (Harvard Apparatus, Edenbridge, KE) at 37° C. during these experiments. A polyethylene catheter (PE50) was inserted into the left common carotid artery. A polyethylene tubing (PE240) was inserted into the trachea and connected to a Fleisch 3.0 pneumotachograph (Whittaker, Blue Bell, Pa.), which was coupled to a Validyne DP45-14 differential pressure transducer (Validyne, Northridge, Calif.). Another PE 190 tubing was placed into esophagus. Transpulmonary pressure, as the difference between the tracheal and esophageal pressure, was detected by a Validyne MPXIIDP differential transducer. The mean blood pressure (MBP) and the heart rates (HR) were derived from the input signal of blood pressure. The respiratory parameters, including tidal volume ($V_T$), respiratory frequency (RF), minute volume ($V_E$), lung resistance ($R_L$) and dynamic lung compliance ($C_{dys}$) were derived from the input signals of flow and the transpulmonary pressure. These data were captured by a Buxco LS-20 system with a PC 486 computer.

Rats (n=3–4/group) were pretreated with either 0.9% saline (1 ml/kg, i.p.) or mecamylamine (1 mg/kg, i.p.) 10 minutes before administration of l-epibatidine (10 μg/kg, s.c.) or nicotine (2 mg/kg, s.c.). Blood pressure, heart rate, and pulmonary functions were monitored during whole experiment.

After nicotine administration (2 mg/kg, s.c.) in anesthetized rats, the cardiovascular and pulmonary responses included hypertension or biphasic changes of blood pressure, depressed breath frequency, and increased tidal volume. Epibatidine (10 μg/kg, s.c.) mimicked these nicotine-induced changes. Mecamylamine (1 mg/kg, i.p.) also blocked l-epibatidine-induced respiratory responses and changes in blood pressure (FIG. 4).

Development of Tachyphylaxix:

The tachyphylaxis was assessed in mice by pretreatment with either l-epibatidine (15 μg/kg s.c.) or nicotine (5 mg/kg s.c.) at either 10 minutes, 3 or 16 hours (N=7/group) before a secondary injection. The mice were tested for antinociception 5 minutes after epibatidine administration and 2 minutes after administration of nicotine.

Figure 5:
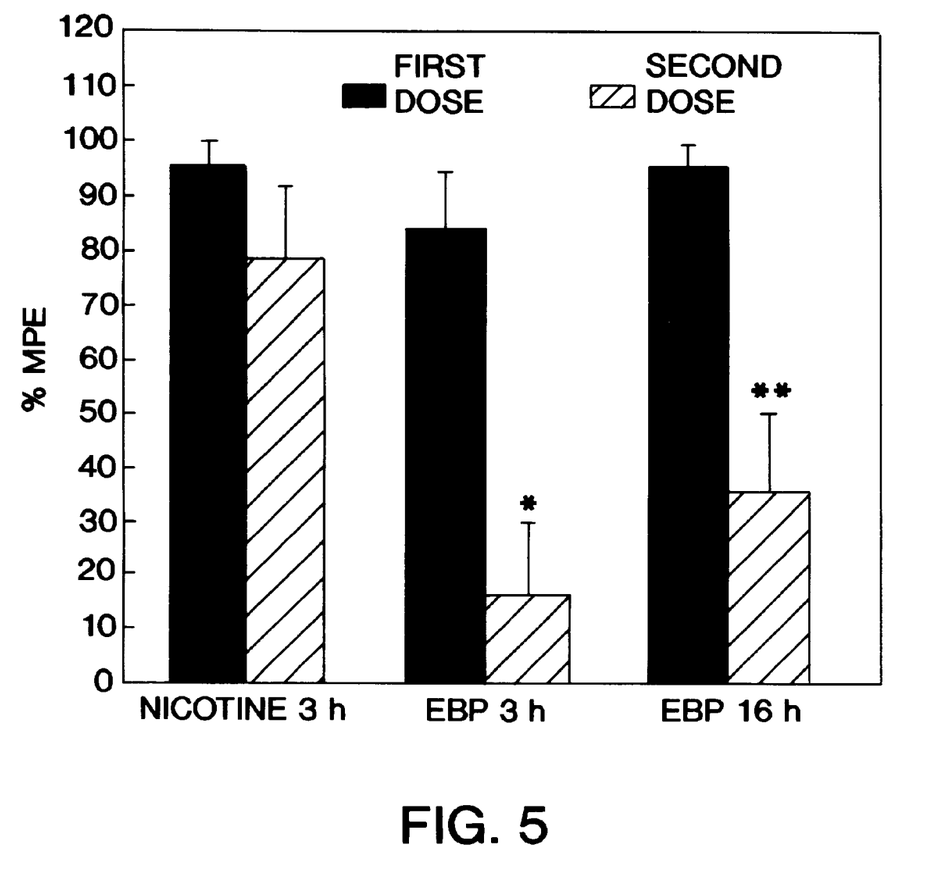
FIG. 5 is a bar chart graph comparing the development of tachyphylaxis to nicotine or epibatidine in mice at intervals of 3 hours (nicotine) and at 3 hours and 16 hours (l-epibatidine). The asterisks indicate the level of significant difference from the first dose effect (*$P<0.05$; **$P<0.01$).

The animals receiving nicotine twice at 3 hour intervals showed no tachyphylaxis, whereas those receiving l-epibatidine at both 3 hour and 16 hour intervals developed tachyphylaxis (FIG. 5).

TABLE I

Analgesic Effects of Epibatidine and Derivatives in the Tail-Flick Assay in Mice

| Compound | Dose Range (μg/kg, s.c.) | $ED_{50}$ value at 5 minutes (μg/kg) |
|---|---|---|
| CMI-488 (d) | 5–50 | 7 |
| CMI-489 (racemic) | 10–50 | 9 |

TABLE I-continued

Analgesic Effects of Epibatidine and Derivatives
in the Tail-Flick Assay in Mice

| | | |
|---|---|---|
| CMI-477 (1) | 5–50 | 9 |
| CMI-545 | 5–50 | 10 |
| CMI-526 | 50–200 | 127 |
| CMI-495 | 100–500 | 285 |
| CMI-492 | 500–1000 | 726 |

STRUCTURES OF TEST COMPOUNDS

CMI-492

CMI-477

CMI-495

CMI-488

CMI-526

CMI-489

CMI-545 racemic

TABLE II

Antagonism of epibatidine antinociception in mice

| Drugs | Dose (mg/kg) | % MPE mean | SE | P value* |
|---|---|---|---|---|
| 0.9% NaCl | 1 | 95 | 3 | |
| mecamylamine | 1 | 4 | 2 | <0.001 |
| hexamethonium | 3 | 50 | 18 | <0.05 |
| naloxone | 3 | 82 | 13 | <0.05 |
| yohimbine | 3 | 69 | 17 | <0.05 |
| atropine | 3 | 94 | 6 | <0.05 |

* As compared with vehicle (0.9% NaCl) effect.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method for treating a disease that can be treated with a nicotinic agonist comprising administering an effective amount of a 7-azabicyclo-heptane or heptene compound having the formula:

wherein:

R[1] and R[4] are independently selected from the group consisting of hydrogen; alkyl; alkylhydroxy; alkyloxyalkyl; alkylthioalkyl; alkylamino; oxyalkyl; carboalkoxy, alkyl; aryl; thioalkyl; and Q;

each R[3], R[5] and R[6] may be independently selected from the group consisting of hydrogen; alkyl; alkylhydroxy; alkyloxyalkyl; alkylthioalkyl; alkylaminoalkyl; oxyalkyl; thioalkyl; halo; —CF$_3$; —NH$_2$; alkylamino; dialkylamino; —CO$_2$H; —CO$_2$-alkyl; —C(O)alkyl; —CH; —C(O)NH$_2$; —C(O)NH(alkyl); —C(O)N(alkyl)$_2$; alkyl; and —SO$_n$(alkyl), —SO$_n$(aryl), —SO$_n$(heteroaryl), wherein n=0, 1 or 2;

R[5] and R[6] together can be alkylidene or haloalkylidene;

each R[2] may be independently selected from the group consisting of hydrogen, alkyl; —CH$_2$—; HC=CH$_2$; alklhydroxy; alkyloxyalkl; alkylamine; caboxylate, —CH; Q; —C(O)Q; and -alkyl(Q);

wherein Q is selected from the group consisting of:

and wherein the Q moiety can be optionally substituted with from 1 to 3 substituent groups W;

wherein each substituent group W is selected from the group consisting of alkyl; halo; heteroaryl; —OH; oxyalkyl; —SH; thioalkyl; —SO(alky); —SO$_2$(alkyl); —OCH$_2$CH=CH$_2$; —OCH$_2$(C$_6$H$_5$); —CF$_3$; —CN; alkylenedioxy; —CO$_2$H; —CO$_2$alkyl; —OCH$_2$CH$_2$OH; —NO$_2$; —NH$_2$; —NH(alkyl); —N(alkyl)2; —NCH(O)alkyl; —SO$_2$CF$_3$; and —NHCH$_2$aryl;

R[7] is selected from the group consisting of hydrogen; alkyl; —CH$_2$—(cycloalkyl); —CH$_2$CH=CH$_2$; —CH$_2$CH$_2$(C$_6$H$_5$); alkylhydroxy; alkylanino(alkyl)$_{0-2}$; alkoxyalkyl; alkylthioalkyl; and aryl; and Q;

wherein the lines—represent optional double bonds in the formula; and pharmaceutically acceptable derivatives and salts thereof.

2. The method of claim 1, wherein:

R[1] and R[4] are independently selected from the group consisting of —H; —CH$_3$; —CH$_2$OH; —CH$_2$OCH$_3$; —CH$_2$SCH$_3$; CH$_2$NHCH$_3$; —CH$_2$N(CH$_3$)$_2$; —OCH$_3$; —SCH$_3$, and Q;

each R[3], R[5] and R[6] may be independently selected from the group consisting of —H; —CH$_3$; —CH$_2$OH; —CH$_2$OCH$_3$; —CH$_2$SCH; —CH$_2$NH$_2$; —CH$_2$NHCH3; —CH$_2$N(CH$_3$)$_2$; —OCH$_3$; SCH$_3$; —Cl; —CF$_3$; —NH$_2$; —N(CH$_3$)2; —NHCH$_3$; —CO$_2$H; —CO$_2$CH$_3$—; —CH; —C(O)NH$_2$; —C(O)NCH$_3$; —C(O)N(CH$_3$)$_2$; —SO$_n$(CH$_3$), —SO$_n$(C$_6$H$_5$), —SO$_n$(C$_5$H$_5$), wherein n—0, 1, 2;

R[5] and R[6] together can be —CH$_2$— and —CF$_2$—;

each R[2] may be independently selected from the group consisting of —H; —CH$_3$; —CH$_2$—; —HC=CH$_2$; —CH$_2$—OH; —CH$_2$O—(CH$_3$); —CH$_2$NH$_2$; —CH; —Q; —C(O)Q; and —CH$_2$(Q);

wherein Q is selected from the group consisting of:

and wherein the Q moiety can be optionally substituted with from 1 to 3 substituent groups W;

wherein each substituent group W is selected from the group consisting of alkyl; halo; aryl; heteroaryl; —OH; oxyalkyl; —SH; thioalkyl; —SO(alkyl); —SO$_2$alkyl; —OCH$_2$CH=CH$_2$; —OCH$_2$(C$_6$H$_5$); —CF$_3$; —CN; alkylenedioxy; —CO$_2$H; —CO$_2$alkyl; —OCH$_2$CH$_2$OH; —NO$_2$; —NH$_2$; —NH(alkyl); —N(alkyl)$_2$, —NCH(O)alkyl; —SO$_2$CF$_3$; and —NHCH$_2$aryl);

R[7] is selected from the group consisting of hydrogen; alkyl; —CH$_2$-cycloalkyl); —CH$_2$CH=CH$_2$; —CH$_2$CH$_2$(C$_6$H$_5$); alkyihydroxy, alkylamino-(alkyl)$_{0-2}$; alkoxyalkyl; alkylthioalkyl; and aryl.

3. The method of claim 1, wherein:

R[1] and R[4] are independently selected from the group consisting of —H; —CH$_3$; —CH$_2$OH; —CH$_2$OCH$_3$; —CH$_2$SCH$_3$; —CH$_2$NHCH$_3$; —CH$_2$N(CH$_3$)$_2$; —OCH$_3$; —C(O)OCH$_3$; —SCH$_3$, and Q;

each R[3], R[5] and R[6] may be independently selected from the group consisting of —H; —CH$_3$; —CH$_2$OH; —CH$_2$OCH$_3$; —CH$_2$SCH$_3$; —CH$_2$NH$_2$; —CH$_2$NHCH3; —CH$_2$N(CH$_3$)$_2$; —OCH$_3$; SCH$_3$; —Cl; —CF$_3$; —NH$_2$; —N(CH$_3$)2; —NHCH$_3$; —CO$_2$H; —CO$_2$CH$_3$; —C(O)CH$_3$; —CH; —C(O)NH$_2$; —C(O)NCH$_3$; —C(O)N(CH$_3$)$_2$; —SO$_n$(CH$_3$), —SO$_n$(C$_6$H$_5$), —SO$_n$(C$_5$H$_{5N}$), wherein n=0, 1, 2;

R[5] and R[6] together can be —CH$_2$— and —CF$_2$—;

each R[2] may be independently selected from the group consisting of —H; —CH$_3$; —CH$_2$—; —HC=CH$_2$; —CH$_2$—OH; —CH$_2$O—(CH$_3$); —CH$_2$NH$_2$; —CH; —Q; —C(O)Q; and —CH$_2$(Q);

wherein Q is selected from the group consisting of:

and wherein the Q moiety can be optionally substituted with from 1 to 3 substituent groups W;

wherein each substituent group W is selected from the group consisting of —$CH_3$; —Cl; —Br, —F; —$C_6H_5$; —$C_5H_5N$; —OH; —$OCH_3$; —SH; —$SCH_3$; —$SOCH_3$; —$SO_2CH_3$; —$OCH_2CH=CH_2$; —$OCH_2(C_6H_5)$; —$CF_3$; —CN; —$CO_2H$; —$CO_2CH_3$; —$OCH_2CH_2OH$; —$NO_2$; —$NH_2$; —$NHCH_3$; $N(CH_3)_2$; —$NHC(O)CH_3$; —$SO_2CF_3$; and —$NHCH_2(C_6H_5)$;

$R^7$ is selected from the group consisting of —H; —$CH_3$; —$CH_2$-(cycloalkyi); —$CH_2CH=CH_2$; —$CH_2CH_2(C_6H_5)$; —$CH_2CH_2OH$; $CH_2CH_2N(CH_3)_2$; —$CH_2OCH_3$; —$CH2SCH_3$; and —$C_6H_5$.

4. The method of claim 1 wherein the nicotinic agonist induces body weight loss.

5. The method of claim 1 wherein the disease is ulcerative colitis or apthous ulcer.

6. The method of claim 1 wherein the disease is smoking.

7. The method of claim 1 wherein the disease is selected from the group consisting of Parkinson's disease, Tourette's syndrome, Alzheimer's disease, ulcerative colitis and apthous ulcer.

8. A method of agonizing the human central nervous system nicotinic receptor $N_n$, comprising administering to a human patient an effective nicotinic agonist amount of a compound selected from the group consisting of CMI-488, CMI-489; CMI-477; CMI-526; CMI-495; CMI-492; CMI-493; CMI-494; and CMI-496, in a physiologically acceptable carrier, wherein the effective amount ranges from about 0.1 to about 20 µg/kg body weight of the patient.

9. A method of agonizing the human nicotinic cholinergic receptor $N_m$, comprising administering to a human patient an effective nicotinic agonist amount of a compound selected from the group consisting of CMI-488, CMI-489; CMI-477; CMI-526; CMI-495; CMI-492; CMI-493; CMI-494; and CMI-496, in a physiologically acceptable carrier, wherein the effective amount ranges from about 0.1 to about 20 µg/kg body weight of the patient.

10. A method of agonizing the human nicotinic cholinergic receptor $M_1$, and $M_2$ comprising administering to a human patient an effective nicotinic agonist amount of a compound selected from the group consisting of CMI-488, CMI-489; CMI-477; CMI-526; CMI-495; CMI-492; CMI-493; CMI-494; and CMI-496, in a physiologically acceptable carrier, wherein the effective amount ranges from about 0.1 to about 20 µg/kg body weight of the patient.

* * * * *